US00PP13956P29

(12) United States Plant Patent
Olsthoorn

(10) Patent No.: US PP13,956 P2
(45) Date of Patent: Jul. 8, 2003

(54) SPATHIPHYLLUM PLANT NAMED 'SWEET DARIO'

(75) Inventor: Petrus C. M. Olsthoorn, Monster (NL)

(73) Assignee: Pothos Plant B.V., Honselersdijk (NL)

( * ) Notice: Subject to any disclaimer, the term of this patent is extended or adjusted under 35 U.S.C. 154(b) by 0 days.

(21) Appl. No.: 10/076,584

(22) Filed: Feb. 19, 2002

(51) Int. Cl.[7] ..... A01H 5/00
(52) U.S. Cl. ..... Plt./364
(58) Field of Search ..... Plt./364

(56) References Cited

PUBLICATIONS

UPOV–ROM GTITM Computer Database 2002/03, GTI Jouve Retrieval Software, Citation for Spathiphyllum 'Sweet Dario'.*

* cited by examiner

*Primary Examiner*—Bruce R. Campell
*Assistant Examiner*—June Hwu
(74) *Attorney, Agent, or Firm*—Foley & Lardner

(57) ABSTRACT

A new and distinct Spathiphyllum plant named 'Sweet Dario' characterized by dark and glossy leaves, high shoots, most shoots producing inflorescences, shell-shaped inflorescences with large spadix.

2 Drawing Sheets

Latin name of the genus and species of the plant claimed: Spathiphyllum hybrid.

Variety denomination: 'Sweet Dario'.

BACKGROUND OF THE INVENTION

The present invention relates to a new and distinct cultivar of Spathiphyllum plant, hereinafter referred to by the cultivar name 'Sweet Dario'. The new cultivar originated from a cross made in a controlled breeding program in Monster, The Netherlands. The female parent is '991274-26' (unpatented). The male parent is '93161-95' (unpatented). 'Sweet Dario' was discovered and selected by the inventor, Petrus C. M. Olsthoorn, as a flowering plant within the progeny of the stated cross in a controlled environment in Monster, The Netherlands.

Asexual reproduction of the new cultivar was first performed by tissue culture in week 16 of 1997 in Honselersdijk, The Netherlands and has demonstrated that the combination of characteristics as herein disclosed for the new cultivar are firmly fixed and retained through successive generations of asexual reproduction and reproduce true-to-type.

BRIEF DESCRIPTION OF THE INVENTION

The following traits have been repeatedly observed and are determined to be basic characteristics of 'Sweet Dario' which in combination distinguish this Spathiphyllum as a new and distinct cultivar:

1. Dark and glossy leaves;
2. Most shoots producing inflorescences;
3. Shell-shaped inflorescence; and
4. Large spadix.

'Sweet Dario' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Honselersdijk, The Netherlands under conditions which closely approximate those generally used in commercial practice.

Of the many commerical cultivars known to the present inventor, the most similar in comparison to 'Sweet Dario' is the cultivar 'Cupido' (unpatented). Compared to 'Cupido', the leaves of 'Sweet Dario' are much darker and glossier. 'Sweet Dario' produces much more shoots than 'Cupido'. About 9 seeds of 'Cupido' are needed to produce the same amount of shoots from a single plant of 'Sweet Dario'. Nearly all shoots of 'Sweet Dario' produce inflorescences whereas only the main shoots of 'Cupido' produce inflorescences. The inflorescences of 'Sweet Dario' are approximately 10 percent bigger than the inflorescences of 'Cupido'. The inflorescence shape of 'Sweet Dario' is shell-shaped whereas the inflorescence shape of 'Cupido' is more oval. The spadix of 'Sweet Dario' is approximately 10–15% larger than the spadix of 'Cupido'. The inflorescence stem of 'Sweet Dario' is also much darker than the inflorescence stem of 'Cupido'. In order to force the shoots of a Spathiphyllum to flower gibberalic acid is added. 'Cupido' needs more than twice the concentration of this hormone than 'Sweet Dario' to get the same result. The main vein of the leaves of 'Sweet Dario' is lighter than the color of the leaves whereas the main vein of the leaves of 'Cupido' is the same color as the leaves. Finally, 'Cupido' is more sensitive to light than 'Sweet Dario' causing the leaves of 'Cupido' to lighten in color faster than those of 'Sweet Dario'.

BRIEF DESCRIPTION OF THE DRAWINGS

The accompanying photographic drawings show a 30-week old plant of 'Sweet Dario' with colors as true as possible with drawings of this type.

The first drawing shows a 'Sweet Dario' plant on the left and a close-up of its inflorescence to the right.

The second drawing shows a 'Sweet Dario' plant on the left and the comparison variety, 'Cupido', on the right.

DETAILED BOTANICAL DESCRIPTION

The following observations, measurements and values describe the new cultivar at 30 weeks as grown in Honselersdijk, The Netherlands under conditions which closely approximate those generally used in commercial practice. Grown in standard glasshouses in well-drained cocos with pH values in cocos/peat soil (50/50) is 6.0–6.2 and 5.8–6.0 in potting soil. Base fertilizing (PG-mix) is 0.75 kgs in cocos/peat soil as well as in potting soil. This species needs careful fertilizer treatment; mixes of calcium nitrate, iron chelate (EDDHA and DTPA), magnesium sulphate, mono potassium phosphate, potassium nitrate, borax, manganese, molybdenum and copper sulphate. Ideal growing conditions under which this plant is grown is 21–23 degrees Celsius during the day and 20 degrees Celsius at night. For flower initiation 'Sweet Dario' gets 60 ppm of gibberalic acid (depending on the pot size, plant development and age of plant). Color references are made to The Royal Horticultural Society Colour Chart (R.H.S.), except where general colors of ordinary significance are used. Color values were taken under daylight conditions at approximately noon in Boskoop, The Netherlands.

Origin: Honselersdijk, The Netherlands, November 2001.

Parentage:

*Male parent.*—'91274-26'.

*Female parent.*—'93161-95'.

Classification:

*Botanical.*—Spathiphyllum.

*Commercial.*—Spathiphyllum cv. Sweet Dario.

Propagation: By tissue culture.

Plant:

*Appearance.*—Broad upright with leaf petioles growing directly from base.

*Height.*—Average 70 cm.

*Width.*—Average 80 cm.

*Growth habit.*—Moderately vigorous.

*Time of flowering.*—18 weeks after potting of a 20 cm cutting.

*Winter hardiness.*—USDA Zone 10.

*Stems.*—Leaves grow directly from base, so no stems are visible.

*Roots.*—Time to initiate roots: 1–2 weeks under 21–23 degrees Celsius (day) and 20 degrees Celsius at night. Time to develop roots: 3–4 weeks under 21–23 degrees Celsius (day) and 20 degrees Celsius at night. Rooting habit: Freely branching.

Foliage:

*Shape.*—Narrow elliptic to lanceolate.

*Apex.*—Acute to slightly apiculate.

*Base.*—Attenuate.

*Texture.*—Smooth, glossy, thin but somewhat leathery.

*Leaf color.*—Upper surface: Closest to green RHS 139A. Lower surface: Green RHS 137C.

*Midrib color.*—Upper Surface: Yellow-green RHS 144A. Lower Surface: Yellow-green RHS 144D.

*Size of leaf.*—Width: Average 12.4 cm. Length: Average 40 cm. Petiole: Average length 40 cm, average diameter 4 mm, petiole rounded to somewhat flattened, color green; RHS 143A.

*Petiole sheath.*—Average 20 cm long and 4 mm wide (measured at halfway point).

*Geniculum.*—Average length 3 cm, average width 6 mm, color green RHS 143C.

*Veins.*—Average 12 pairs of furrowed secondary veins, upper side color yellow-green RHS 144A, under side color green RHS 137B to RHS 137C.

Inflorescence description:

*Immature.*—Peduncle: Average length 53 cm, average diameter 3 mm, rounded, green in color RHS 144A to RHS 144B. Spathe: Average length 11 cm, average width 4.5 cm, cupped, average depth 1.5 cm.

*Mature.*—Spathe: Size: Average length 13 cm, average width 5.5 cm, only slightly cupped, average depth 1 cm. Color: Unopened Bud: White closest to RHS 155A. Fully Open: Front Surface: White closest to RH 155A, midrib green RHS143C. Back Surface: White closest to RHS 155A, midrib green RHS 143B. Apex: Apiculate, green RHS 143A. Faded: Front Surface: Brown RHS 199A. Back Surface: Brown RHS 199A to RHS 199B. Apex: Apiculate.

*Arrangement.*—Solitary.

*Shape.*—Broad lanceolate, base decurrent.

*Margins.*—Entire.

*Fragrance.*—Sweet, faint.

*Lastingness of the individual inflorescence.*—On average over two weeks.

Reproductive organs:

*Spadix.*—Size: Average length 5.5 cm, average width 1.3 cm. Quantity: Average 140 individual flowers per spadix. Color: Greyed-yellow RHS 160D. Stamens: 6, pressed against styles. Pistil: Each individual flower has one pistil with a tri-parted stigma; the pistil has an average length of 2 mm, color greyed-yellow RHS-160D.

*Pollen.*—Yellow-white RHS 158A, plenty produced.

Seed production: No observation to date.

Fruit production: No observation to date.

Disease resistance/susceptibility: No observation to date.

I claim:

1. A new and distinct Spathiphyllum plant named 'Sweet Dario', substantially as illustrated and described herein.

* * * * *

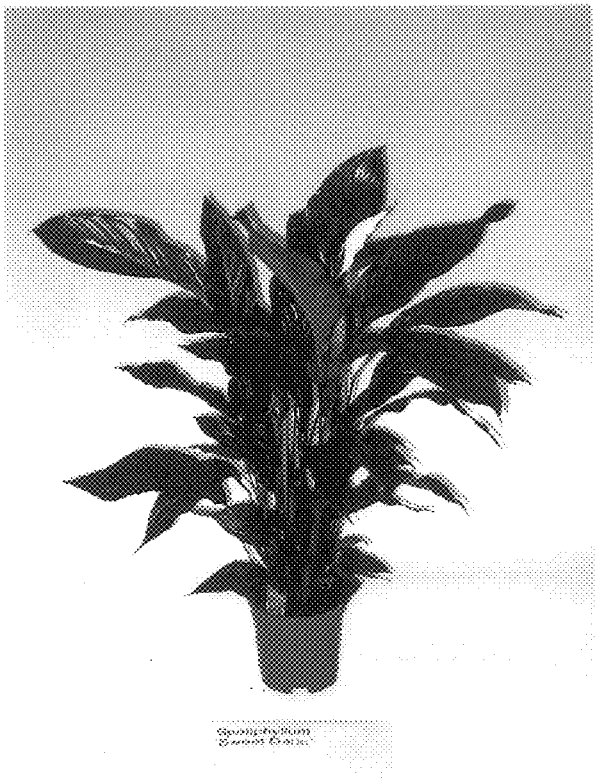
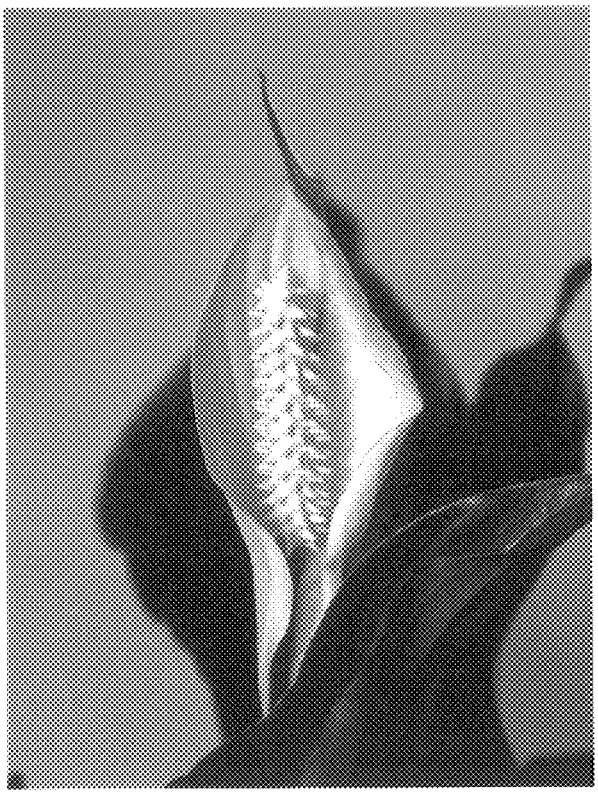

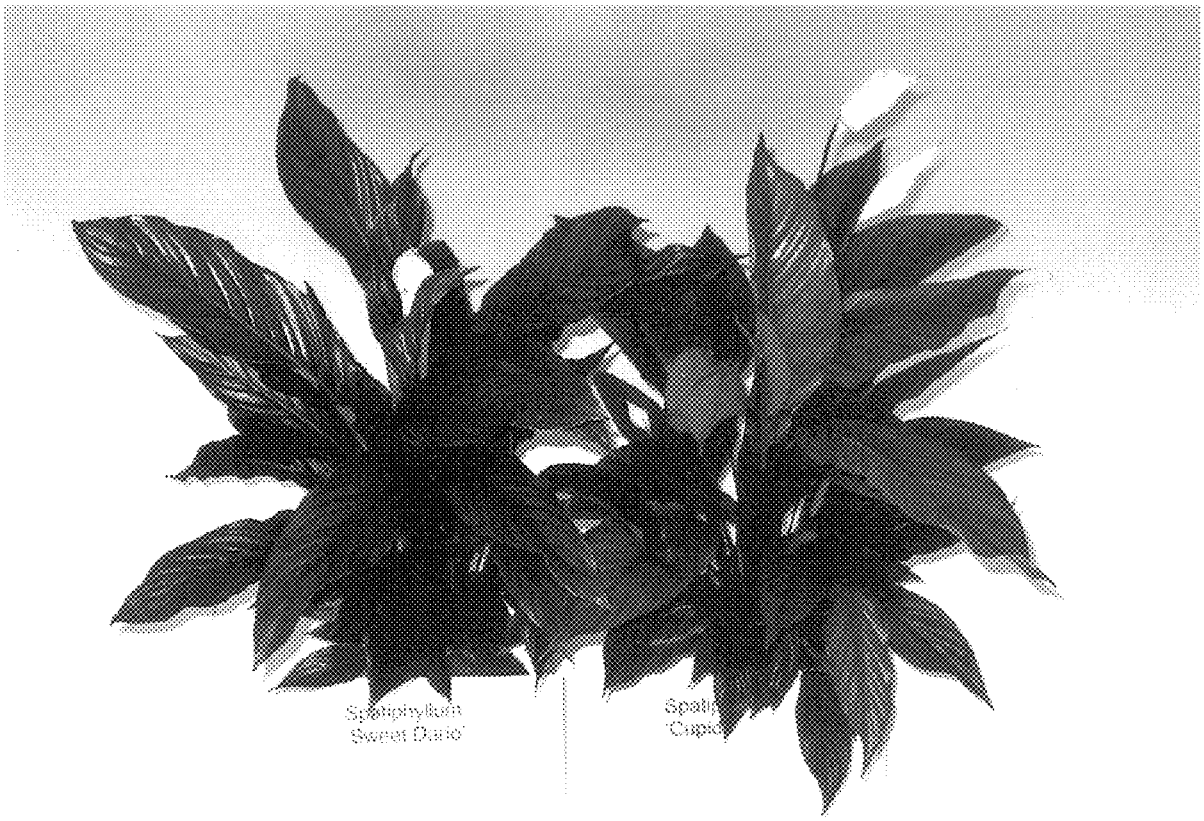
Spathiphyllum
'Sweet Dario'
Spati
'Cupid